United States Patent
Fourie et al.

(10) Patent No.: US 7,312,045 B2
(45) Date of Patent: Dec. 25, 2007

(54) AGGRECANASE-1 AND -2 PEPTIDE SUBSTRATES AND METHODS

(75) Inventors: Anne M. Fourie, San Diego, CA (US); Lars Karlsson, La Jolla, CA (US); Fawn Coles, Cardiff, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 11/012,797

(22) Filed: Dec. 15, 2004

(65) Prior Publication Data

US 2005/0164319 A1     Jul. 28, 2005

Related U.S. Application Data

(63) Continuation of application No. 10/050,200, filed on Jan. 16, 2002, now abandoned.

(51) Int. Cl.
*C12Q 1/37* (2006.01)
*C12N 9/64* (2006.01)
*A61K 38/00* (2006.01)
*A61K 38/04* (2006.01)

(52) U.S. Cl. .................. 435/23; 435/226; 530/327; 530/300

(58) Field of Classification Search .............. 435/23, 435/226; 530/327, 300
See application file for complete search history.

(56) References Cited

OTHER PUBLICATIONS

Tortorella et al. The trombospondin motif of aggrecanase-1 (ADAMTS-4) is critical for aggrecan substrate recognition and cleavage, J. Biol. Chem. Aug. 18, 2000, 275/33, pp. 25791-25797.*
Supplementary Partial European Search Report dated Nov. 15, 2005 for corresponding Appln. No. 03 70 2145.
Horber C. et al."Truncation of the Amino-Terminus of the Recombinant Aggrecan rAgg1mut Leads to Reduced Cleavage at the Aggrecanase Site. Efficient Aggrecanase Catabolism May Depend on Multiple Subtrate Interactions." Matrix Biology: Journal of the International Society for Matrix Biology Nov. 2000, vol. 19, No. 6, Nov. 2000 pp. 533-543, XP002350412.
Mercuri F.A. et al."Mutations in the Interglobular Domain of Aggrecan Alter Matrix Metalloproteinase and Aggrecanase Cleavage Patterns. Evidence that Matrix Metalloproteinase Cleavage Interferes with Aggrecanase Activity" The Journal of Biological Chemistry, Oct. 20, 2000, vol. 275, No. 42, XP002350413.
Fosang A.J. et al.: Aggrecan is Degraded By Matrix Metalloproteinases in Human Arthiritis: Evidence That Matrix Metalloproteinase and Aggrecanase Activities Can Be Independent Journal of Clinical Investigation, New York, NY USA, vol. 98, No. 10, Nov. 1996 XP001183906.

* cited by examiner

*Primary Examiner*—Rebecca E. Prouty
*Assistant Examiner*—Malgorzata A. Walicka

(57) ABSTRACT

The present invention describes synthetic peptide substrates of the metalloproteases, aggrecanase-1 and/or -2 suitable for assays of enzyme activity. The invention also describes methods using these peptides to discover pharmaceutical agents that modulate these proteases.

9 Claims, 5 Drawing Sheets

A. Full length Aggrecanase-1 protein

B. Full length Aggrecanase-2 protein

C. Recombinant truncated form

AGGRECANASE-1 AND -2 PEPTIDE SUBSTRATES AND METHODS

This is a continuation of application Ser. No. 10/050,200, filed Jan. 16, 2002, now abandoned, the entire contents of which are incorporated by reference.

FIELD OF THE INVENTION

The present invention describes synthetic peptide substrates of the metalloproteases, aggrecanase-1 and/or -2, suitable for use in assays of enzyme activity. The invention also describes methods using these peptides to discover pharmaceutical agents that modulate these proteases.

BACKGROUND OF THE INVENTION

The disintegrin metalloprotease (or ADAM) family of cell surface proteolytic enzymes is known to play roles in sperm-egg binding and fusion, muscle cell fusion, neurogenesis, modulation of Notch receptor and ligand processing, and processing of the pro-inflammatory cytokine, TNFα (Primakoff and Myles, *Trends Genet* 16:83-87, 2000). The ADAMs have been shown to consist of pre-, pro-, protease, disintegrin-like-, cysteine-rich, epidermal growth factor-like, transmembrane, and cytoplasmic domains. Members of a novel sub-family of the ADAMs, the ADAMTS proteins, lack the transmembrane domain and contain unique thrombospondin motifs, believed to mediate their binding to the extracellular matrix (Tang and Hong, *FEBS Lett.* 445:223-225, 1999). Two members of the ADAMTS family, namely ADAMTS-4 and -5 (also referred to as ADAMTS-11), have been shown to be capable of aggrecan cleavage. Aggrecan is the major proteoglycan of cartilage (Abbaszade et al., *J. Biol. Chem.* 274:23443-23450, 1999; Tortorella et al., *Science* 284:1664-1666, 1999). As a result, these proteins have been implicated in the cartilage damage associated with osteoarthritis and inflammatory joint disease, and have been named "aggrecanase-1" (Genbank Accession NM 005099) and "aggrecanase-2" (Genbank NM 007038), respectively.

Aggrecanases and matrix metallo proetinases (MMPs) have been shown to cleave aggrecan at a number of different sites (Pratta et al., *J. Biol. Chem.* 275:39096-39102, 2000; Sandy et al., *Biochem. J.* 351:161-166, 2000; Tortorella et al., *J. Biol. Chem.* 275:18566-18573, 2000). Products resulting from cleavage of aggrecan at the site Glu373-Ala374, in the interglobular domain of aggrecan, have been shown to accumulate in synovial fluid of patients with osteoarthritis and inflammatory joint disease (Lohmander et al., *Arthritis Rheum.* 36:1214-22, 1993). Aggrecanase-1 and -2, but not MMPs, are able to cleave aggrecan at this site. A 40 amino acid peptide representing the sequence of aggrecan surrounding the aggrecanase cleavage site (PCT Publication Number WO 00/05256) was able to serve as a substrate for aggrecanase enzymatic activity; however, no peptides less than 40 amino acids in length functioned as suitable substrates for aggrecanase activity, suggesting that shorter substrates, such as substrates of 20 amino acids in length, would not work. Minimum size limits for aggrecanase substrates are consistent with studies suggesting that aggrecanase activity is sensitive to the amino terminal truncation of aggrecan (Horber et al., *Matrix Biol.* 19:533-543, 2000). Glycosylation of the aggrecan substrate has also been shown to affect aggrecanase activity (Pratta et al., *J. Biol. Chem.* 275:39096-39012, 2000).

A sensitive and specific assay for the aggregan degrading metalloproteases, suitable for high-throughput screening, would be helpful in identifying inhibitors of these enzymes for potential therapeutic agents against cartilage damage associated with osteoarthritis and inflammatory joint disease. This invention relates to amino acid peptides shorter than 40 amino acids, unrelated to the aggrecan sequence, but containing aggrecanase sensitive sites, and their use in assays suitable for high throughput screening (HTS) formats.

SUMMARY OF THE INVENTION

The present invention relates to peptides less than 40 amino acids in length having a cleavage site between a glutamic acid on the N-terminal side of the cleavage site and a non-polar or uncharged residue on the C-terminal side of the cleavage site and wherein the peptide is cleavable by an enzyme having an amino acid sequence of SEQ ID NO:8 (truncated aggrecanase-1) and/or SEQ ID NO:9 (truncated aggrecanase-2). In one aspect of this embodiment, the peptide comprises the amino acid sequence of SEQ ID NO:3 and SEQ ID NO:4. Preferably the peptide is of natural or synthetic origin. In a preferred aspect of this embodiment, the peptide comprises a detectable label selected from the group consisting of $^{125}I$, $^{131}I$, $^{3}H$, $^{14}C$, $^{35}S$, $^{32}P$, $^{33}P$, a fluorescent dye, or a colorimetric indicator. The peptide preferably also comprises a fluorophore and a quencher or acceptor located at opposite ends of the cleavage site of the peptide. In one embodiment, the peptide further comprises an affinity moiety located at opposite ends of the cleavage site of the peptide.

In another embodiment, the invention relates to a method to identify a compound that inhibits aggrecanase enzymatic activity comprising the steps of: contacting a test compound, an aggrecanase, and a peptide less than 40 amino acids in length wherein the peptide comprises a cleavage site between a glutamic acid on the N-terminal side of the cleavage site and a non-polar or uncharged amino acid residue on the C-terminal side of the cleavage site and wherein the peptide is cleavable by an enzyme having the amino acid sequence of SEQ ID NO:8; and detecting cleavage of the peptide, wherein inhibition of peptide cleavage in the presence of a test compound indicates compound inhibition of aggrecanase enzymatic activity. In a preferred aspect of this embodiment, the method is performed in a single reaction vessel. Preferably the enzyme is selected from the group consisting of aggrecanase-1 or aggrecanase-2. Preferably the peptide is selected from the group consisting of SEQ ID NO:3, SEQ ID NO:4, SEQ ID NO:5, SEQ ID NO:6 and SEQ ID NO:7. Preferably the peptide further comprises a detectable label selected from the group consisting of $^{125}I$, $^{131}I$, $^{3}H$, $^{14}C$, $^{35}S$, $^{32}P$, $^{33}P$, a fluorescent dye, or a colorimetric indicator. The peptide preferably further comprises a fluorophore and a quencher or acceptor located at opposite ends of the cleavage site of the peptide. In one aspect of this embodiment, the contacting step further comprises a cell expressing the aggrecanase.

In another aspect of this invention, the invention relates to a method to detect the ability of a compound to inhibit aggrecanase-1 or -2 enzymatic activity comprising the steps of: contacting a test compound, an aggrecanase secreted by a cell, and a peptide having an amino acid sequence selected from the group consisting of SEQ ID NO:3 or SEQ ID NO:4; incubating the compound, enzyme, and peptide to permit enzymatic cleavage of the peptide; and measuring enzymatic cleavage of the peptide wherein the method is conducted in a single reaction vessel without further manipulation. Preferably the peptide comprises a detectable label selected from the group consisting of $^{125}$I, $^{131}$I, $^3$H, $^{14}$C, $^{35}$S, $^{32}$P, $^{33}$P, a fluorescent dye, or a colorimetric indicator. Also preferably, the peptide comprises a fluorophore and a quencher or acceptor located at opposite ends of the cleavage site of the peptide.

In yet another aspect of this invention, the invention relates to a method to identify a compound capable of inhibiting aggrecanase activity comprising the steps: providing a peptide comprising an affinity moiety, an amino acid sequence selected from a group consisting of SEQ ID NO3 SEQ ID NO:4 and a detectable label, said affinity moiety and label located on opposite sides of a cleavage site encoded by the amino acid sequence; contacting the peptide with an affinity capture coated solid phase support for sufficient time to bind a portion of the peptide; washing the support to remove unbound peptide; contacting a solution comprising a test compound and functional enzyme with the peptide bound solid phase support for sufficient time to allow enzymatic cleavage of the peptide, thereby releasing the peptide and detectable label into the solution; and measuring changes in the quantity of the detectable label as a result of compound modulation of expected enzymatic function. Preferably the enzyme is selected from the group consisting of aggrecanase-1 and -2. Also preferably the peptide comprises a detectable label selected from the group consisting of $^{125}$I, $^{131}$I, $^3$H, $^{14}$C, $^{35}$S, $^{32}$P, $^{33}$P, a fluorescent dye, or a colorimetric indicator.

BRIEF DESCRIPTION OF THE DRAWINGS

In FIG. 2, every other peptide is numbered.

FIG. 4 illustrates the use of the aggrecanase-1 and -2 peptide cleavage assays to identify inhibitory compounds.

DETAILED DESCRIPTION OF THE INVENTION

Figure 1:
FIG. 1 illustrates the domain structures of (A) full-length aggrecanase-1 protein, (B) full-length aggrecanase-2 protein and (C) the recombinant truncated forms used in a preferred protease assay of this invention.
Figure 1:
Figure 1:

In one aspect of this invention, the invention relates to peptide substrates useful to measure the enzymatic activity of aggrecanase-1 and/or -2 metalloproteases. Using the peptide substrates identified in this invention it is possible to find others that are capable of being cleaved by the preferred truncated aggrecanase-1 and -2 enzymes of this invention. Preferred recombinant truncated forms of human aggrecanase-1 and -2 (i.e., aggrecanase lacking some portion of the complete native sequence), in this invention were creating using the pro- and protease domains and optionally included a FLAG epitope tag, as provided in schematic in FIG. 1 (and provided as nucleic acid encoding the truncated aggrecanse, see SEQ ID Nos: 1 and 2 respectively). These recombinant truncated enzymes were produced from Sf9 cells infected with a recombinant baculovirus construct, and purified by affinity chromatography. A number of substrates were identified by screening a collection of 56 potential peptide substrates. Two different peptide sequences were found that were particularly preferred for their ability to be cleaved by truncated aggrecanase-2. One peptide sequence was a good substrate for both truncated aggrecanase-1 and truncated aggrecanase-2. This latter peptide was used to optimize an assay in a format suitable for high throughput screening, which was then used for the identification of small molecule inhibitors of aggrecanase-1 and -2 as potential therapeutic compounds.

The amino acid sequence of the most preferred peptides is provided in single letter code in Table 1.

TABLE 1

Relative activities of AGGRECANASE-1 AND -2 for 2 different FRET peptides

| SEQ ID NO: | Peptide name | Peptide sequence | Relative proteolytic Activity | |
|---|---|---|---|---|
| | | | Agg-1 | Agg-2 |
| 3 | FasL1 | Aedans-E-KELAELRESTS-Dabcyl-K | * | ***** |
| 4 | 29CD23 | Aedans-E-ADLSSFKSQEL-Dabcyl-K | n.d. | ***** |

(n.d. = not detectable)

These peptides and the other peptides of this invention demonstrating aggrecanase substrate activity are useful in assays to discover new pharmaceutical drugs that alter the activity of aggrecanase-1 and/or -2.

The invention also relates to assays using the peptides of this invention to detect compounds that inhibit aggrecanase enzymatic activity. In one aspect of this embodiment, the assay is a homogeneous in vitro protein-based assay to detect compound modulation of aggrecanase-1 and/or -2 enzymatic activity.

The term "homogeneous" refers to an assay conducted in a single vessel where there is no further reagent manipulation after the reaction reagents are placed in a vessel. A preferred method comprises the steps of;

1) combining a test compound with an aggrecanase and a peptide substrate, 2) incubating the compound, enzyme, and substrate for a time sufficient to detect substrate cleavage; and 3) detecting substrate cleavage.

In a preferred embodiment, the detecting step comprises detecting a change in the level of substrate cleavage. Preferably the change in the level of substrate cleavage is compared to the change in the level of substrate cleavage in a reaction vessel containing aggrecanase and peptide substrate in the presence of a control test compound that has a known capacity or no capacity to inhibit aggrecanase activity or alternatively in a reaction vessel without test compound.

Figure 2:
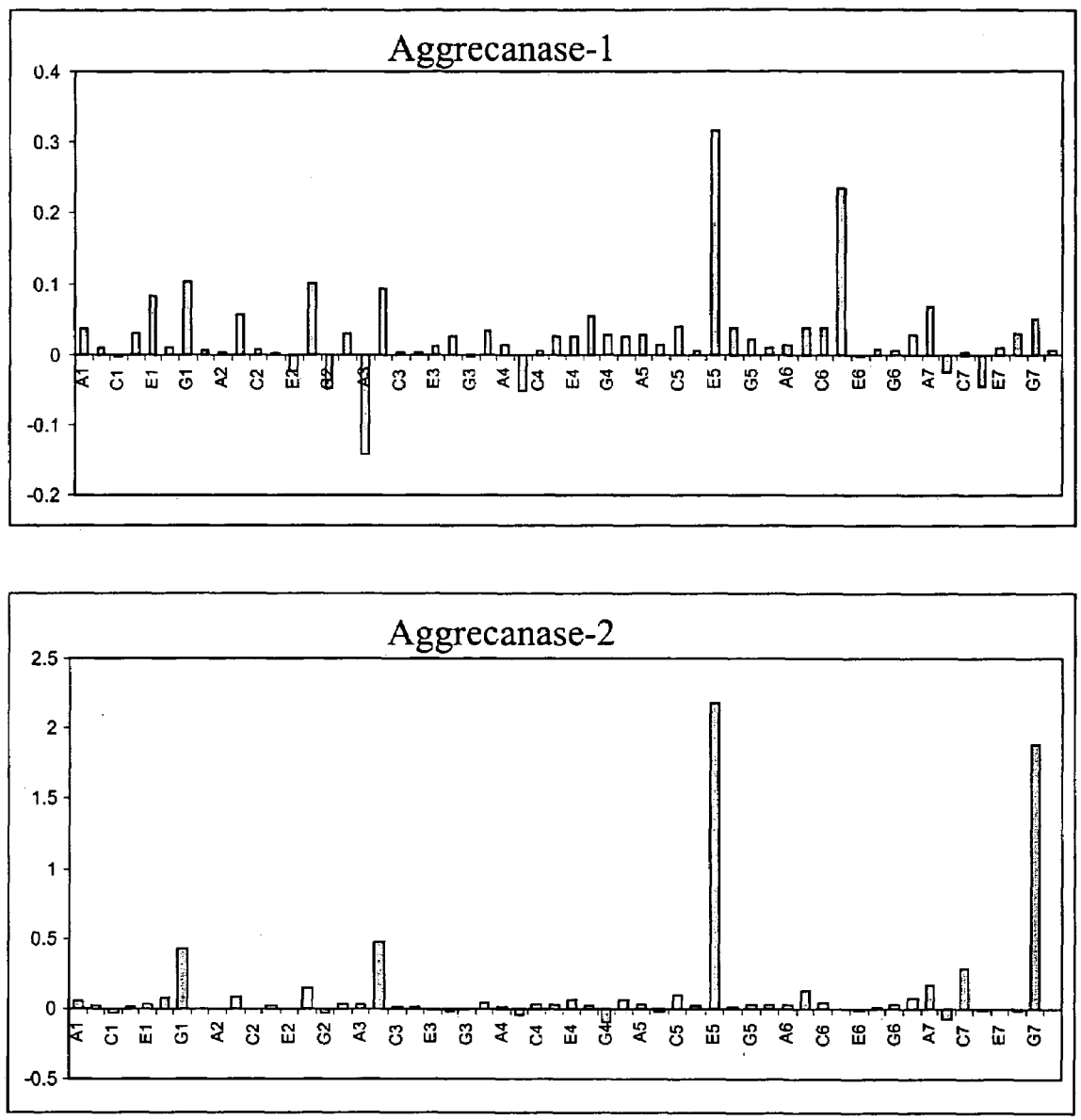
FIG. 2 illustrates the relative activities of aggrecanase-1 (A) and -2 (B) for 56 different fluorescent resonance energy transfer (FRET) peptides, A1 to H7.

In a preferred embodiment, the peptide substrate is selected from SEQ ID NO:3 (E5 in FIG. 2) or SEQ ID NO:4 (G7 in FIG. 2).

Other preferred peptides that can serve as peptides substrates in the assays of this invention for aggrecanase-2 include, but are not limited to:

| ID from FIG. 2 | Sequence | SEQ ID NO |
|---|---|---|
| G1 | Aedans-EKARVLAEAADabcyl-Kamide | 5 |
| B3 | Aedans-EKARVLAEAMDabcyl-Kamide | 6 |
| C7 | Aedans-ERAEQQRLKSQDLDabcyl-Kamide | 7 |

Still other peptides tested are provided in Table 3. In addition, a variety of peptides can also serve as substrates for aggrecanase-1 and/or -2 activity. For example, the present set of peptide substrates was selected by identifying other protease substrates known in the art. The peptides included a collection of substrates for other proteases, as well as a number of sequences corresponding to membrane proximal cleavage sites of various proteins postulated to be released by metalloproteases (including those published by Roghani et al., *J. Biol. Chem.* 274:3531-340, 1999) for ADAM9/MDC9). Thus, those of ordinary skill in the art could similarly identify other substrates and test them in the assays of this invention using a truncated aggrecanase as contemplated here.

The term truncated "aggrecanase" as used herein refers to a truncated enzyme (as shown in FIG. 1) that displays enzymatic cleavage of a peptide substrate, and for which the corresponding full-length enzyme is known to have the capacity to cleave aggrecan. Efficient cleavage of aggrecan depends on multiple interactions between the enzyme and aggrecan. For example, cleavage depends on an intact N-terminal portion of the substrate, aggrecan (Horber et al., *Matrix Biology* 19:533-543, 2000). Tortorella et al. (*J. Biol. Chem.* 275:25791-25797, 2000) showed that cleavage of aggrecan was dependent on the thrombospondin motif in the enzyme, aggrecanase-1, although both full-length and truncated aggrecanase-1 could cleave a peptide substrate (quoted as unpublished data). Currently known aggrecanases are aggrecanase-1 and -2 (Genbank Accession Nos. NM 005099 and NM 007038 respectively). Nucleic acid encoding the truncated versions of these enzymes used in the assays of this invention are provided here as SEQ ID NOS:1 and 2, corresponding to truncated aggrecanase-1 and truncated aggrecanase-2, respectively.

While the aggrecanases used in this invention are truncated forms of a full length native aggrecanase provided by the GenBank citations above, other aggrecanases can be used in this invention as long as they retain their ability to cleave exemplary peptides SEQ ID NO:3 and SEQ ID NO:4. The aggrecanases used in this invention can be full length, partial, truncated, chimeric or modified enzymes that still retain their ability to cleave the peptides as described in this invention. It has been demonstrated that aggrecanase cleavage sites in aggrecan contain glutamic acid on the N-terminal side of the cleavage site (P1 position) and a non-polar or uncharged residue on the C-terminal side of the cleavage site (P1' position), namely alanine, leucine or glycine (Caterson et al., *Matrix Biology* 19:333-344, 2000; Tortorella et al., *J. Biol. Chem.* 275 18566). As shown later under Kinetic Analysis in Example 2, the truncated aggrecanase-2 used in the assays described here cleaves the peptides of SEQ ID NOS: 3 and 4 between glutamic acid and leucine residues, consistent with the cleavage specificity of aggrecan cleavage sites.

The term "compound" is used herein in connection with a small molecule, preferably an organic molecule that has the potential to disrupt the specific enzymatic activity of the enzyme. For example, but not to limit the scope of the current invention, compounds may include small organics, synthetic or natural amino acid peptides, proteins, synthetic or natural nucleic acid sequences, or any chemical derivatives of the aforementioned. The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as *Remington: The Science and Practice of Pharmacy.* 1995. Mack Publishing Co. ISBN 0912734051.

The methods described herein are especially useful for high throughput screening (HTS) of compounds to discover compounds that modulate aggrecanase function. The term "high throughput" refers to an assay design that allows easy analysis of multiple samples simultaneously, and capacity for robotic manipulation. Preferred assays are homogeneous assays. Preferred assays also include assay designs that are optimized to reduce reagent usage in order to achieve the analysis desired. The methods described herein demonstrate highly robust performance and good linearity as a function of enzyme concentration and substrate concentration. For example in the assays of the present invention, at appropriately adjusted enzyme and substrate concentrations, the assay was linear for up to four hours. From FIG. 4A, it can be seen that for kinetic analysis, the signal-to-noise ratio was effectively infinite, as no change in the background (blank, no enzyme) was observed over the time of the assay. For endpoint measurements, the enzyme and substrate concentrations can be adjusted to achieve the desired signal-to-noise ratio. In the example in FIG. 4A, it can be seen that this ratio (control versus blank endpoints) was approximately three. Therefore the amount of reagent used can be varied to utilize a minimum of expensive reagent, such as a recombinant enzyme.

Examples of assay formats include 96-well or 384-well plates, levitating droplets, and "lab on a chip" microchannel chips used for liquid handling experiments. For example, capillary electrophoresis (CE)-based assays for the activity of proteases have been developed. In this type of system, the assays can be carried out in small volumes (<5 µl). Here both the fluorescent-labeled substrate and product can be monitored by laser-induced fluorescence, based on the ability of CE to rapidly separate the two species.

It is well known to those in the art that as miniaturization of plastic molds and liquid handling devices are advanced, or as improved assay devices are designed, that greater numbers of samples may be performed using the design of the present invention. Such new assay designs will not limit the scope of the intended assay.

In another embodiment of the invention, the present invention provides a homogeneous in vitro cell-based method to detect compound modulation of aggrecanase enzymatic activity. In this embodiment, the cells express aggrecanase and the peptide substrate and test compound are in contact with aggrecanase. Aggrecanase is preferably released extracellularly. In a preferred embodiment, the aggrecanase is an aggrecanase-1 or an aggrecanase-2. The method comprises the steps of:

1) combining a test compound, a cell expressing aggrecanase, and a peptide substrate; and 2) detecting enzymatic cleavage of the peptide substrate.

Alternatively the assays of this invention could be made non-homogeneous. That is, the assay could be modified to require more than one vessel or a wash step requiring that all events to do not take place in a single reaction sample. Such assays can involve, for example, the immobilization of the substrate peptide. One example is the use of an affinity moiety—affinity capture pair such as streptavidin capture of a biotinylated substrate peptide. Affinity capture pairs are well known in the art and include, for example, avidin/biotin, antibody capture of a region of the substrate peptide, and polyhistidine/immobilized nickel. A preferred non-homogeneous method comprises the steps of:

1) providing a substrate peptide comprising an affinity moiety, an aggrecanase cleavage site, and a detectable label, said affinity moiety and label located on opposite sides of the cleavage site;

2) contacting the substrate peptide with an affinity capture coated solid phase support for sufficient time to bind a portion of the peptide;

3) washing the support to remove unbound peptide;

4) contacting a solution comprising a test compound and aggrecanase enzyme with the peptide bound solid phase support for sufficient time to allow enzymatic cleavage of the substrate, thereby releasing the substrate and detectable label into the solution; and 5) measuring changes in the quantity of the detectable label as a result of compound modulation of expected aggrecanase enzymatic function.

In one embodiment, the aggrecanase is aggrecanase-1 and/or -2. In another embodiment, the solution is transferred to a reaction vessel prior to the measuring step. The terms solid phase support, affinity capture, unbound versus bound peptide, and the like are all well-known terms to those of ordinary skill in the art to whom this invention pertains and therefore these definitions will not be repeated here.

A change in the quantity of product can be expressed as the total amount of product changing over time (a stop-time assay) or can be kinetic where a change in the enzymatic rate is measured as a function of time. Kinetic assays are preferably measured from the time of initial contact of the enzyme and substrate to a point in time where approximately 50% of the maximum observed product is generated.

The amount of expected aggrecanase enzymatic activity can be determined by running, concurrently or separately, an assay using a compound that does not inhibit enzymatic function (i.e., a blank or a control compound), or with a solvent vehicle that has similar properties as that used for the test compound but lacks any test compound, such as DMSO, DMF, or isopropyl alcohol.

For cell-based assays, the amount of time necessary for cellular contact with the compound is empirically determined, for example, by running a time course with a known aggrecanase modulator and measuring change as a function of time.

Cells useful in the cell-based aggrecanase assays of this invention are those cells that naturally express aggrecanase, or cells transfected with recombinant aggrecanase. These cells may be immortalized cell lines or primary culture cells from any mammal, preferably murine, rat, rabbit, monkey, chimpanzee, or human.

Methods for detecting compounds that modulate aggrecanase proteolytic activity comprise combining a test compound with an aggrecanase protein and a suitable labeled substrate and detecting the ability of the enzyme to cleave the substrate in the presence of the compound. Enzymatic cleavage can result in release of the label or release of a labeled peptide fragment that can be distinguished from intact labeled peptide. In one example, the substrate is labeled. A variety of methods for exploiting labeled substrates are known in the art. Examples of different types of labeled substrates include, for example, substrate that is radiolabeled (Coolican et al., *J. Biol. Chem.* 261:4170-76, 1986), fluorometric (Twining, *Anal. Biochem.* 143:30-4, 1984) or colorimetric (Buroker-Kilgore and Wang, *Anal. Biochem.* 208:387-392, 1993) substrates.

Radioisotopes useful in the present invention include those well known in the art, specifically $^{125}I$, $^{131}I$, $^{3}H$, $^{14}C$, $^{35}S$, $^{32}P$, and $^{33}P$. Radioisotopes are introduced into the peptide by conventional means, such as iodination of a tyrosine residue, phosphorylation of a serine or threonine residue, or incorporation of tritium, carbon or sulfur utilizing radioactive amino acid precursors. Fluorescent resonance energy transfer (FRET)-based methods (Ng and Auld, *Anal. Biochem.* 183:50-6, 1989) can also be used to detect compounds that modulate aggrecanase proteolytic activity. Compounds that are activators will increase the rate of substrate degradation resulting in a reduction in substrate as a function of time. Compounds that are inhibitors will decrease the rate of substrate degradation and will result in greater remaining substrate as a function of time.

A preferred assay format useful for the method of the present invention is a FRET-based method using peptide substrates that contain a fluorescent donor with either a quencher or acceptor that are separated by a peptide sequence encoding the aggrecanase cleavage site. A fluorescent donor is a fluorogenic compound that can absorb energy and transfers a portion of the energy to another compound. Examples of fluorescent donors suitable for use in the present invention include, but are not limited to, coumarins, xanthene dyes such as fluoresceines, rhodols, and rhodamines, resorufins, cyanine dyes bimanes, acridines, isoindols, dansyl dyes, aminophthalic hydrazides such as luminol and isoluminol derivatives, aminonapthalimides, aminobenzofurans, aminoquinolines, dicanohydroquinones, and europium and terbium complexes and related compounds. A quencher is a compound that reduces the emission from the fluorescent donor when it is appropriately proximally located to the donor. Preferred quenchers do not generally re-emit the energy in the form of fluorescence. Examples of quenching moieties include indigos, benzoquinones, anthraquinones, azo compounds, nitro compounds, indoanilines, and di- and triphenylmethanes.

A FRET method using a donor/quencher pair measures increased emission from the fluorescent donor as a function of aggrecanase enzymatic activity upon the peptide substrate. Therefore a test compound that antagonizes aggrecanase will generate an emission signal between two control samples—a low (basal) fluorescence from the FRET peptide alone and a higher fluorescence from the FRET peptide digested by the activity of enzymatically active aggrecanase. An acceptor is a fluorescent molecule that absorbs energy from the fluorescent donor and re-emits a portion of the energy as fluorescence. An acceptor is a specific type of quencher that enables a separate mechanism to measure aggrecanase proteolytic efficacy. Methods that use a donor/acceptor pair measure a decrease in acceptor emission as a function of aggrecanase enzymatic activity upon the peptide substrate. Therefore a test compound that antagonizes aggrecanase will generate an emission signal between two control samples—a higher basal fluorescence from the FRET peptide alone and a lower fluorescence from the FRET peptide digested by the activity of enzymatically active aggrecanase. Examples of acceptors useful in the methods of the present invention include, but are not limited to, coumarins, fluoresceins, rhodols, rhodamines, resorufins, cyanines, difluoroboradiazindacenes, and phthalcyanines. FRET peptides can also be used for zymography (see PCT publication number WO 01/94377 to Fourie et al.) following SDS polyacrylamide gel electrophoresis.

The following examples illustrate the present invention without, however, limiting the same thereto. All references are incorporated herein by reference.

EXAMPLE 1

Generation of Truncated Recombinant Enzyme

Aggrecanase proteins usually comprise: an N-terminal pro-domain and a metalloprotease domain, followed by the disintegrin domain, cysteine-rich domain, epidermal growth factor repeat, thrombospondin repeats and a spacer region, as illustrated in FIG. 1. For production of biologically active and soluble ADAMTS proteins (truncated aggrecanase-1 and -2), PCR products containing the pro- and protease domains and a C-terminal FLAG epitope (used for immunodetection and purification) were cloned into pFastBac 1 (GibcoBRL) vectors using standard techniques. The DNA sequences of truncated aggrecanase-1 and -2 used in the methods of this invention are provided as SEQ ID NOS:1 and 2 respectively. The protein sequences corresponding to these DNA sequences are provided as SEQ ID NOS: 8 and 9.

In order to generate large quantities of protein for biological testing and assay development, Sf9 cells were infected with pFastBac (GibcoBRL) containing the coding sequences for truncated aggrecanase-1 or -2.

Recombinant baculovirus for truncated aggrecanase-1 or -2 expression was generated from the pFastBac1 construct described above using the Bac-to-Bac system (Gibco BRL). Sf9 cells were infected with baculovirus and the medium was collected after 72 hours. The medium was concentrated 10-fold by ultrafiltration, and exchanged to TBS (Tris Buffered Saline) by repeated addition and re-concentration. The supernatant was centrifuged for one hour at 15000×g, filtered through a 0.45 µM filter to remove debris, and incubated, with mixing, overnight at 4° C. with M2-αFlag-agarose (Sigma). The resin was loaded into a column and washed with TBS, followed by elution of the bound material with 0.1M Glycine (pH 3.5) and immediate neutralization by addition of 12.5 µl/ml of 2M Tris-HCl, pH 8. The supernatant from the infection (before and after incubation with M2-αFlag-agarose) and fractions from the purification were analyzed by SDS-PAGE followed by staining and Western blotting. By SDS-PAGE, fractions containing the immunopurified truncated aggrecanase-1 or -2 protein contained a protein band with an apparent molecular weight of about 30 kDa. Western analysis indicated that the M2αFlag (Sigma) antibody identified a 30 kDa band in the infection supernatant before, but not after, anti-FLAG agarose adsorption. The immunoreactive protein was also present in eluted fractions. This protein was then used to test potential substrate peptides.

EXAMPLE 2

Fret Assay

Peptide Substrate Screening

Fifty-six different peptides were synthesized to test for protease activity (see Table 3 below). The peptides included a collection of substrates for other proteases, as well as a number of sequences corresponding to membrane proximal cleavage sites of various proteins postulated to be released by metalloproteases (including those published by (Roghani et al., *J. Biol. Chem.* 274:3531-340, 1999) for ADAM9/MDC9). In order to use the principle of fluorescence resonance energy transfer, or FRET, the peptides were labeled at the C-terminus with Dabcyl and at the N-terminus with Aedans (or vice versa). Thus cleavage of the peptides was monitored by the increase in Aedans fluorescence at 460 nm (excitation 360 nm) as a result of the decrease in proximity of the Dabcyl quencher. The assay was performed by diluting the truncated aggrecanase-1 (approximately 2.5 to 5 µg of protein, 85 to 167 picomoles, SEQ ID NO:8) or truncated aggrecanase-2 (approximately 0.5 to 1 µg of protein, 17 to 33 picomoles, SEQ ID NO:9), in assay buffer (50 mM HEPES pH 7.5, 10 mM $CaCl_2$, 0.1M NaCl and 0.05% (w/v) Brij-35 detergent (Sigma).

The reaction was initiated by the addition of peptide substrate to a final concentration of 100 uM for truncated aggrecanase-1 and 50 uM for truncated aggrecanase-2. The assays were typically run for 60 minutes at room temperature and the slope of the kinetic increase in fluorescence was determined to calculate the rate of the reaction.

FIG. 2 illustrates the relative activities for the 56 different peptides, A1 to H7 (only every alternate peptide is numbered in FIG. 2) expressed in arbitrary, but relative units. Truncated aggrecanase-1 and -2 both showed the highest activity for peptide E5 (FasL1). Truncated aggrecanase-2, but not truncated aggrecanase-1, also showed high activity for cleavage of peptide G7 (29CD23). Peptide D7 (16 amino acids) corresponds to the sequence within aggrecan containing the Glu373-Ala374 aggrecanase cleavage site. Neither truncated aggrecanase-1 nor truncated aggrecanase-2 showed any activity on this peptide, consistent with findings that peptides corresponding to this region of aggrecan, and shorter than 40 amino acids do not function as substrates for aggrecanases (PCT Publication Number WO 00/05256; Horber et al., *Matrix Biology* 19:533-543, 2000).

Peptide E5 (SEQ ID NO:3) was also shown in similar screening assays to be a suitable substrate for the metalloproteases MMP7 and MMP13 (Chemicon, Cat. #CC1059 and CC068 respectively).

Figure 3:
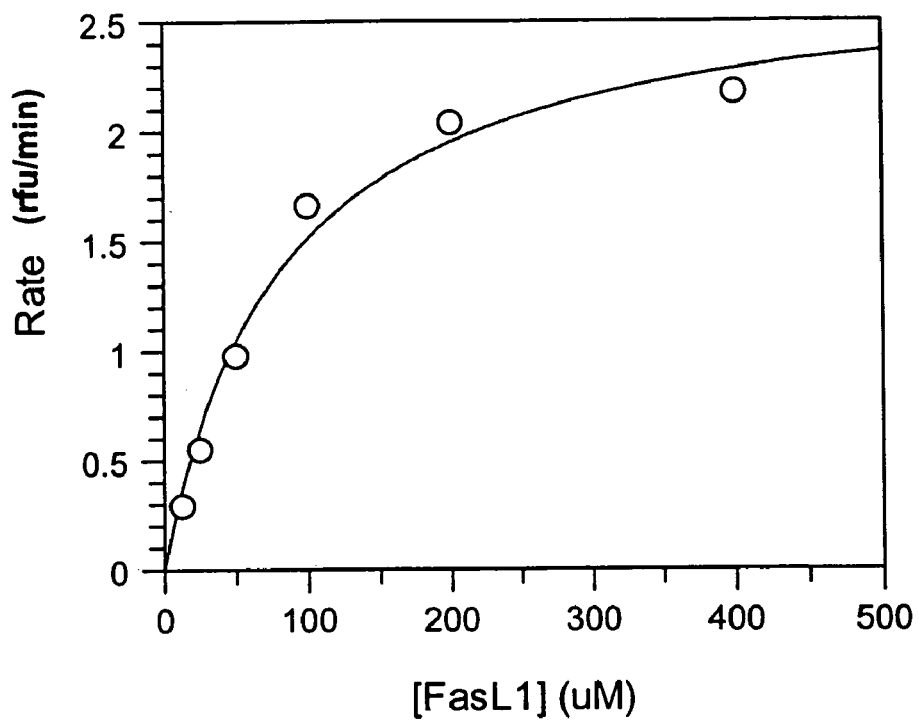
FIG. 3 provides the kinetic analysis of the relative affinities of aggrecanase-2 for cleavage of 2 different peptides
Figure 3:
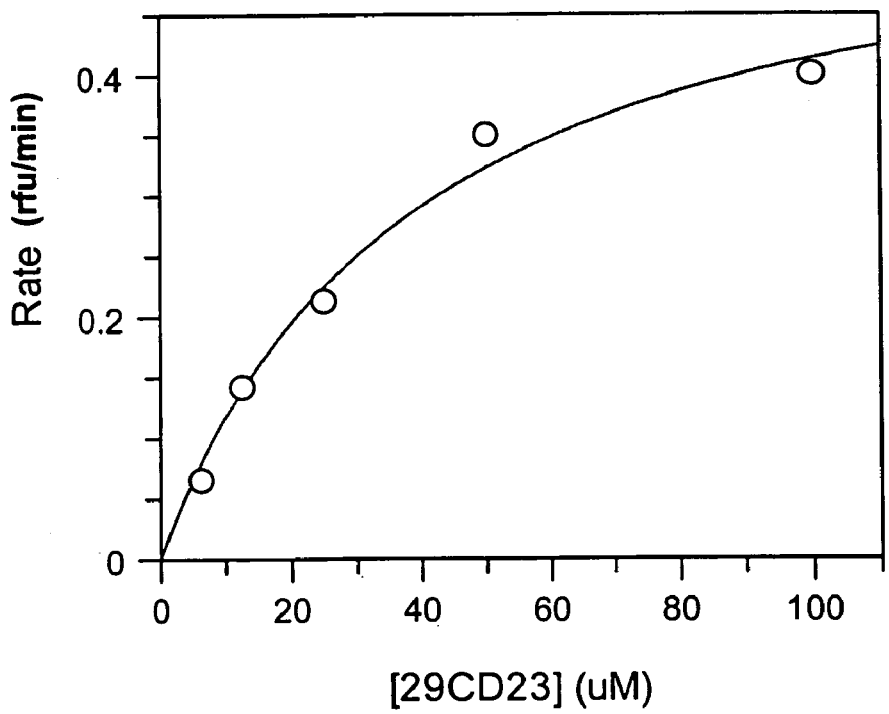

Kinetic Analysis of the Affinity of Aggrecanase-1 and -2 for Cleavage of 4 Different Peptides To confirm the screening assay, aggrecanase-2 was further analyzed for its rate of catalysis using 2 different peptides. The assay was performed by diluting the aggrecanase-2 in assay buffer (50 mM HEPES pH 7.5, 10 mM $CaCl_2$, 0.1M NaCl and 0.05% Brij-35). As illustrated in FIG. 3, the reaction was initiated by the addition of substrate (FasL1 or 29CD23) to different final concentrations for analysis of affinities. The assay was run for 60 minutes at room temperature. FIG. 3 illustrates the proteolytic activity (in relative fluorescence units per minute) as a function of peptide concentration for peptides FasL1 and 29CD23. The curves were fitted to the data with the program Grafit (Erithacus Software Lmited). The results of these analyses are provided in Table 2. The Vmax and Km for each substrate were calculated by non-linear fitting of the data. The cleavage site for aggrecanase-2 within each peptide was determined by LC-MS analysis to be between a glutamic acid and leucine residues in each case, as indicated in Table 2 by a carot within each peptide sequence. These results indicate that the cleavage by the truncated aggrecanase-2 has the same specificity as the full-length enzyme, namely glutamic acid in the P1 position and a non-polar residue in the P1' position. However, these are clearly not the only requirements for efficient cleavage, as a number of the 56 peptides tested have similar residues and were not cleaved by the aggrecanases.

TABLE 2

| $K_m$ and $V_m$ of Aggrecanase -2 for peptides | | | |
|---|---|---|---|
| PEPTIDE | CLEAVAGE SITE | $K_m$ | $V_m$ |
| FasL1 | X-KELAE^LRESTS-Z | 80 µM | 2.8 rfu/min |
| 29CD23 | X-ADLSSFKSQE^L-Z | 40 µM | 0.6 rfu/min |

(X = Aedans-E; Z = Dabcyl-K; rfu = relative fluorescence units)

TABLE 3

| WELL | SEQUENCE | SEQ. ID NO. |
|---|---|---|
| A1 | (Aedans)EHSDAVFTDNYTR(Dabcyl)K-amide | 10 |
| B1 | (Aedans)EAEN(Dabcyl)K-amide | 11 |
| C1 | (Aedans)EGRHIDNEEDI(Dabcyl)K-amide | 12 |
| D1 | (Aedans)EGNAFNNLD(Dabcyl)K-amide | 13 |
| E1 | (Aedans)EYTPNNEIDSF(Dabcyl)K-amide | 14 |
| F1 | (Aedans)EQLRMKLP(Dabcyl)K-amide | 15 |
| G1 | (Aedans)EKARVLAEAA(Dabcyl)K-amide | 5 |
| H1 | (Aedans)ERGFFYTP(Dabcyl)K-amide | 16 |
| A2 | (Aedans)EVTEGPIP(Dabcyl)K-amide | 17 |
| B2 | (Aedans)EPLFYEAP(Dabcyl)K-amide | 18 |
| C2 | (Aedans)ELPMGALP(Dabcyl)K-amide | 19 |
| D2 | (Aedans)EKPAAFFRL(Dabcyl)K-amide | 20 |
| E2 | (Aedans)ELYENKPRRPYIL(Dabcyl)K-amide | 21 |
| F2 | (Aedans)ESEVNLDAEF(Dabcyl)K-amide | 22 |
| G2 | (Aedans)ESQNYPIVQ(Dabcyl)K-amide | 23 |
| H2 | (Aedans)EKPIEFFRL(Dabcyl)K-amide | 24 |
| A3 | (Aedans)EKPAEFFAL(Dabcyl)K-amide | 25 |
| B3 | (Aedans)EKARVLAEAM(Dabcyl)K-amide | 6 |
| C3 | (Aedans)EKPAKFFRL(Dabcyl)K-amide | 26 |
| D3 | R(Aedans)EIPFHLVIHT(Dabcyl)KR | 27 |
| E3 | (Aedans)EMAPGAVHLPQ(Dabcyl)K-amide | 28 |
| F3 | (Aedans)EPLAQAVRSSS(Dabcyl)K-amide | 29 |
| G3 | (Aedans)EPPVAASSLRN(Dabcyl)K-amide | 30 |
| H3 | (Aedans)EPQIENVKGTE(Dabcyl)K-amide | 31 |
| A4 | (Aedans)ESLPVQDSSSV(Dabcyl)K-amide | 32 |
| B4 | (Aedans)EVHHQKLVFFA(Dabcyl)K-amide | 33 |
| C4 | (Dabcyl)KRGVVNASSRLAK(Aedans)E-amide | 34 |
| D4 | (Dabcyl)KLVLASSSF(Aedans)E-amide | 35 |
| E4 | (Dabcyl)KSNRLEASSRSSP(Aedans)E-amide | 36 |
| F4 | (Aedans)EDEMEE(Abu)ASHLPY(Dabcyl)K-amide | 37 |
| G4 | (Aedans)EAGPRGMAGQFSH(Dabcyl)K-amide | 38 |
| H4 | (Dabcyl)KRPLGLAR(Aedans)E-amide | 39 |
| A5 | (Aedans)EGYYSRDMLV(Dabcyl)K-amide | 40 |
| B5 | (Aedans)EQKLDKSFSMI(Dabcyl)K-amide | 41 |
| C5 | (Aedans)EPSAAQTARQHP(Dabcyl)K-amide | 42 |
| D5 | (Aedans)EPGAQGLPGVG(Dabcyl)K-amide | 43 |
| E5 | (Aedans)EKELAELRESTS(Dabcyl)K-amide | 3 |
| F5 | (Dabcyl)GLRTNSFS(Aedans) | 44 |
| G5 | (Dabcyl)RGVVNASSRLA(Aedans) | 45 |
| H5 | Ac-ED(Aedans)KPILFFRLGK(Dabcyl)E-amide | 46 |
| A6 | (Aedans)EMHTASSLEKQIG(Dabcyl)K-amide | 47 |
| B6 | (Aedans)ERFAQAQQQLP(Dabcyl)K-amide | 48 |
| C6 | (Aedans)EKKENSFEMQGDQ(Dabcyl)K-amide | 49 |
| D6 | (Dabcyl)LAQAVRSSSR(Aedans) | 50 |
| E6 | (Aedans)ERTAAVFRP(Dabcyl)K-amide | 51 |
| F6 | (Aedans)ERVRRALP(Dabcyl)K-amide | 52 |
| G6 | (Aedans)ESFPRMFSD(Dabcyl)K-amide | 53 |
| H6 | (Aedans)EEYLESFLERP(Dabcyl)K-amide | 54 |
| A7 | (Aedans)ERPKPQQFFGLM(Dabcyl)K-amide | 55 |
| B7 | (Aedans)EHGDQMAQKSQST(Dabcyl)K-amide | 56 |
| C7 | (Aedans)ERAEQQRLKSQDL(Dabcyl)K-amide | 7 |
| D7 | (Aedans)ERNITEGEARGSVIL(Dabcyl)K-amide | 57 |
| E7 | (Aedans)EAGQRLATAM(Dabcyl)K-amide | 58 |
| F7 | (Aedans)EVGLMGKRALNS(Dabcyl)K-amide | 59 |
| G7 | (Aedans)EADLSSFKSQEL(Dabcyl)K-amide | 4 |
| H7 | (Aedans)EKEDGEARASTS(Dabcyl)K-amide | 60 |

EXAMPLE 3

Drug Screening Assay

Aggrecanase-1 (2.5 to 5 g of protein, 85 to 167 picomoles) was diluted in assay buffer (50 mM HEPES pH 7.5, 10 mM CaCl$_2$, 0.1M NaCl, 0.05% Brij-35). Samples were prepared containing putative inhibitors A (Chen et al. Biorg. Med. Chem. Lett. 6(13):1601-1606, 1996) or B (Bailey, et al. Biorg. Med. Chem. Lett. 9(21):3165-3170, 1999), shown below, at a final concentration of 7.5 micromolar. The final % DMSO in the assay was 3% and it was determined experimentally that this concentration was not detrimental to the activity of the enzyme. The reaction was initiated by the addition of FasL1 peptide substrate to a final concentration of 225 μM and readings were taken at one-minute intervals, for a total of 200 minutes at room temperature.

The assay was always performed at enzyme and substrate concentrations where the activity was linearly related to enzyme concentration and where the increase in fluorescence (reaction rate) was linear for at least the time of the assay. From FIG. 4A, it can be seen that for kinetic analysis, the signal-to-noise ratio is effectively infinite, as no change in the background (blank, no enzyme) is observed over the time of the assay. For endpoint measurements, the enzyme and substrate concentrations could be adjusted to achieve the desired signal-to-noise ratio. In the example in FIG. 4A, it can be seen that this ratio (control versus blank endpoints) was approximately three.

Figure 4A:
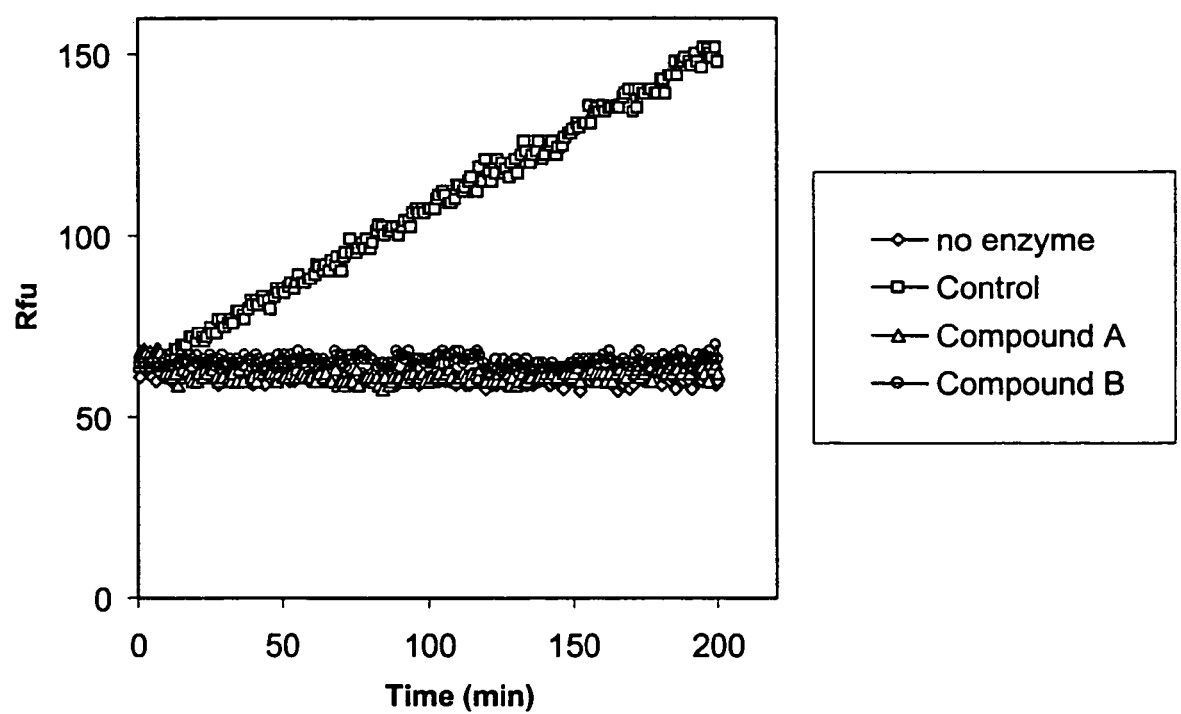
FIG. 4A is a comparison of inhibition of aggrecanase-1 proteolytic activity by compounds A and B.

FIG. 4A shows that inhibitors A and B completely inhibited aggrecanase-1 enzyme activity (results are comparable to blank [no enzyme]).

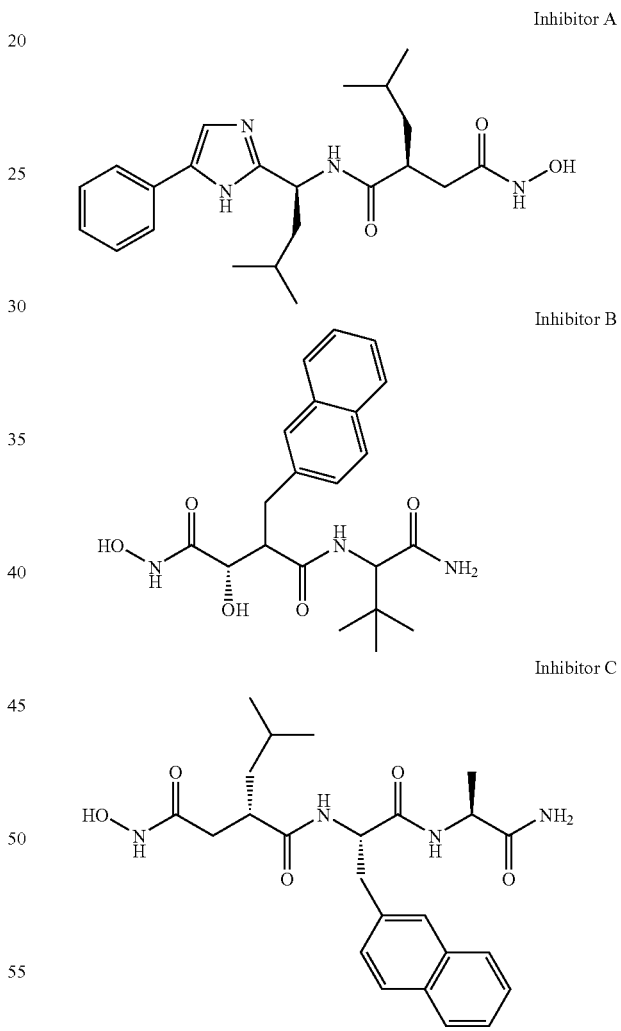

IC50 Analysis for Inhibition of Aggrecanase-2 by Inhibitors A, B, and C

Figure 4B:
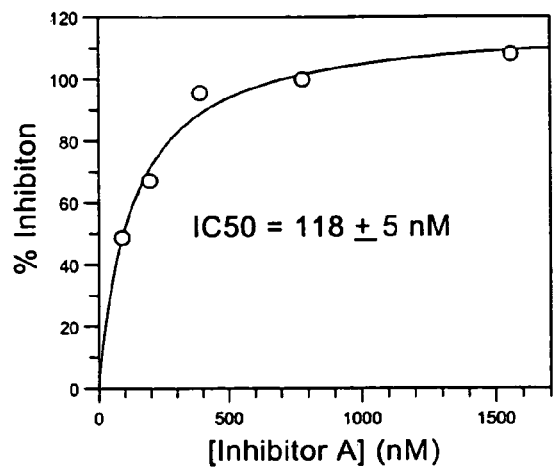
FIG. 4B provides the IC50 analysis for inhibition of aggrecanase-2 by inhibitory compounds, A, B and C.
Figure 4B:
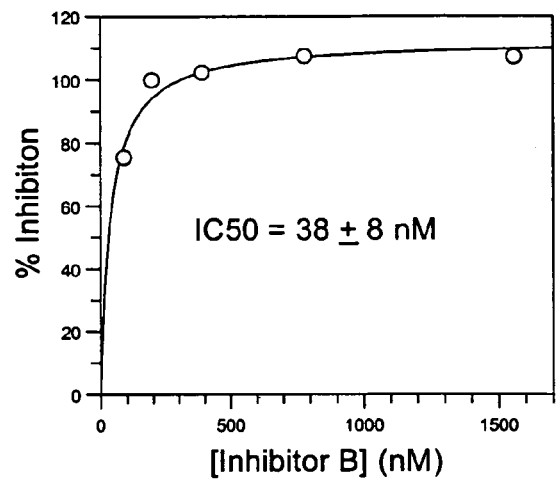
Figure 4B:
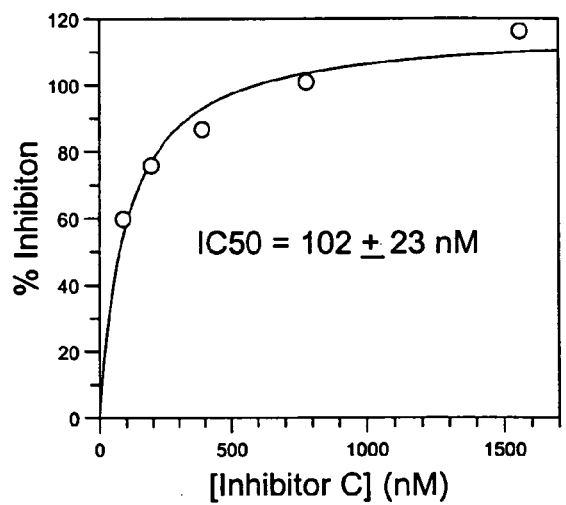

Aggrecanase-2 (0.5 to 1 μg of protein, 17 to 33 picomoles) was diluted in assay buffer (50 mM HEPES pH 7.5, 10 mM CaCl$_2$, 0.1M NaCl, 0.05% Brij-35). Samples were prepared containing Inhibitor A, B or C (shown above) at final concentrations ranging from 0.1 to 12.5 μM (final DMSO concentration of 1.5%). Duplicate assays were run for each concentration of Inhibitor A, B and C (purchased from Peptides International, TAPI-0, Cat. No. INH 3850-P1) for 60 minutes at room temperature. The reaction was initiated by the addition of FasL1 peptide substrate to a final concentration of 225 μM. The reaction rates over 60 minutes at room temperature, in the absence (control) and presence of various concentrations of the inhibitor, were determined by linear regression of the data points. The reaction rate data in FIG. 4B were fitted by non-linear regression using the program Grafit (Erithacus Software). The IC50s for inhibition of Aggrecanase-2 by Inhibitors A, B and C, were 118±5, 38±8, and 102±23 nM, respectively.

What is claimed is:

1. An isolated and purified peptide which is SEQ ID NO:3 or SEQ ID NO:4, having a cleavage site between a glutamic acid on the N-terminal side of the cleavage site and a non-polar or uncharged residue on the C-terminal side of the cleavage site and wherein the peptide is cleavable by an enzyme having the amino acid sequence of SEQ ID NO:8 or SEQ ID NO:9.

2. The peptide of claim 1 wherein the peptide comprises a detectable label selected from the group consisting of $^{125}I$, $^{131}I$, $^{3}H$, $^{14}C$, $^{35}S$, $^{32}P$, $^{33}P$, a fluorescent dye, or a calorimetric indicator.

3. The peptide of claim 1 wherein the peptide comprises a fluorophore and a quencher or acceptor located at opposite ends of the cleavage site of the peptide.

4. The peptide of claim 3 wherein the peptide further comprises an affinity moiety located at opposite ends of the cleavage site of the peptide.

5. A method to identify a compound that inhibits full-length aggrecanase metalloprotease enzymatic activity comprising the steps of:
   contacting a test compound, an aggrecanase, and a peptide having less than 40 amino acids in length and comprising the amino acid sequence of SEQ ID NO:3 or SEQ ID NO:4, wherein the peptide comprises a cleavage site between a glutamic acid on an N-terminal side of the cleavage site and a non-polar or uncharged amino acid residue on a C-terminal side of the cleavage site and wherein the peptide substrate is cleavable by an enzyme having the amino acid sequence of SEQ ID NO:8 or SEQ ID NO:9;
   and detecting cleavage of the peptide, wherein inhibition of peptide cleavage in a presence of a test compound indicates compound inhibition of full length aggrecanase metalloprotease enzymatic activity.

6. The method of claim 5 wherein the method is conducted in a single reaction vessel.

7. The method of claim 5 wherein the full-length aggrecanase is selected from the group consisting of aggrecanase-1 and aggrecanase-2.

8. The method of claim 5 wherein the peptide further comprises a detectable label selected from the group consisting of $^{125}I$, $^{131}I$, $^{3}H$, $^{14}C$, $^{35}S$, $^{32}P$, $^{33}P$, a fluorescent dye, and a colorimetric indicator.

9. The method of claim 5 wherein the peptide further comprises a fluorophore and a quencher or acceptor located at opposite ends of the cleavage site of the peptide.

* * * * *

SEQUENCE LISTING

<160> NUMBER OF SEQ ID NOS: 60

<210> SEQ ID NO 1
<211> LENGTH: 1359
<212> TYPE: DNA
<213> ORGANISM: Homo sapiens

<400> SEQUENCE: 1

| | | | | | |
|---|---|---|---|---|---|
| gaattcgcca | tgtcccagac | aggctcgcat | cccgggaggg | gcttggcagg | gcgctggctg | 60 |
| tggggagccc | aaccctgcct | cctgctcccc | attgtgccgc | tctcctggct | ggtgtggctg | 120 |
| cttctgctac | tgctggcctc | tctcctgccc | tcagcccggc | tggccagccc | cctcccccgg | 180 |
| gaggaggaga | tcgtgtttcc | agagaagctc | aacggcagcg | tcctgcctgg | ctcgggcacc | 240 |
| cctgccaggc | tgttgtgccg | cttgcaggcc | tttggggaga | cgctgctact | agagctggag | 300 |
| caggactccg | gtgtgcaggt | cgagggctg | acagtgcagt | acctgggcca | ggcgcctgag | 360 |
| ctgctgggtg | gagcagagcc | tggcacctac | ctgactggca | ccatcaatgg | agatccggag | 420 |
| tcggtggcat | ctctgcactg | ggatggggga | gccctgttag | gcgtgttaca | atatcggggg | 480 |
| gctgaactcc | acctccagcc | cctggaggga | ggcacccta | actctgctgg | gggacctggg | 540 |
| gctcacatcc | tacgccggaa | gagtcctgcc | agcggtcaag | gtcccatgtg | caacgtcaag | 600 |
| gctcctcttg | gaagccccag | cccagaccc | cgaagagcca | agcgctttgc | ttcactgagt | 660 |
| agatttgtgg | agacactggt | ggtggcagat | gacaagatgg | ccgcattcca | cggtgcgggg | 720 |
| ctaaagcgct | acctgctaac | agtgatggca | gcagcagcca | aggccttcaa | gcacccaagc | 780 |
| atccgcaatc | ctgtcagctt | ggtggtgact | cggctagtga | tcctggggtc | aggcgaggag | 840 |
| gggccccaag | tggggcccag | tgctgcccag | accctgcgca | gcttctgtgc | ctggcagcgg | 900 |
| ggcctcaaca | ccctgaggga | ctcggaccct | gaccactttg | acacagccat | tctgtttacc | 960 |
| cgtcaggacc | tgtgtggagt | ctccacttgc | gacacgctgg | gtatgctga | tgtgggcacc | 1020 |
| gtctgtgacc | cggctcggag | ctgtgccatt | gtggaggatg | atgggctcca | gtcagccttc | 1080 |
| actgctgctc | atgaactggg | tcatgtcttc | aacatgctcc | atgacaactc | caagccatgc | 1140 |
| atcagtttga | atgggccttt | gagcacctct | cgccatgtca | tggcccctgt | gatggctcat | 1200 |
| gtggatcctg | aggagccctg | gtcccctgc | agtgcccgct | tcatcactga | cttcctggac | 1260 |
| aatggctatg | ggcactgtct | cttagacaaa | ccagaggctc | cattgcatct | gcctgtgact | 1320 |
| ggggactaca | aggacgacga | tgacaagggg | taggtcgac | | | 1359 |

<210> SEQ ID NO 2
<211> LENGTH: 1516
<212> TYPE: DNA
<213> ORGANISM: Homo sapiens

<400> SEQUENCE: 2

| | | | | | |
|---|---|---|---|---|---|
| gtcgacgcag | cgcactatgc | tgctcgggtg | ggcgtccctg | ctgctgtgcg | cgttccgcct | 60 |
| gccctggcc | gcggtcggcc | ccgccgcgac | acctgcccag | gataaagccg | ggcagcctcc | 120 |

```
gactgctgca gcagccgccc agccccgccg gcggcagggg gaggaggtgc aggagcgagc      180
cgagcctccc ggccacccgc acccctggc gcagcggcgc aggagcaagg ggctggtgca       240
gaacatcgac caactctact ccggcggcgg caaggtgggc tacctcgtct acgcgggcgg      300
ccgcaggttc ctcttggacc tggagcgaga tggttcggtg ggcattgctg gcttcgtgcc      360
cgcaggaggc gggacgagtg cgccctggcg ccaccggagc cactgcttct atcggggcac      420
agtggacggt agtccccgct ctctggctgt ctttgacctc tgtggggtc tcgacggctt       480 cttcgcggtc aagcacgcgc gctacaccct aaagccactg ctgcgcggac cctgggcgga     540
ggaagaaaag gggcgcgtgt acgggatgg gtccgcacgg atcctgcacg tctacacccg       600
cgagggcttc agcttcgagg ccctgccgcc gcgcgccagc tgcgaaaccc ccgcgtccac     660
accgagggcc cacgagcatg ctccggcgca cagcaacccg agcggacgcg cagcactggc     720
ctcgcagctc ttggaccagt ccgctctctc gcccgctggg ggctcaggac cgcagacgtg     780
gtggcggcgg cggcgccgct ccatctcccg ggcccgccag gtggagctgc ttctggtggc    840
tgacgcgtcc atggcgcggt tgtatggccg gggcctgcag cattacctgc tgaccctggc    900
ctccatcgcc aataggctgt acagccatgc tagcatcgag aaccacatcc gcctggccgt    960
ggtgaaggtg gtggtgctag cgacaaggga caagagcctg gaagtgagca agaacgctgc   1020
caccacactc aagaactttt gcaagtggca gcaccaacac aaccagctgg agatgaccca    1080
tgaggagcac tacgatgcag ctatcctgtt tactcgggag gatttatgtg gcatcattc     1140 atgtgacacc ctgggaatgg cagacgttgg gaccatatgt tctccagagc gcagctgtgc    1200
tgtgattgaa gacgatggcc tccacgcagc cttcactgtg gctcacgaaa tcggacattt    1260
acttggcctc tcccatgacg attccaaatt ctgtgaagag acctttggtt ccacagaaga    1320
taagcgctta atgtcttcca tccttaccag cattgatgca tctaagccct ggtccaaatg    1380
cacttcagcc accatcacag aattcctgga tgatggccat ggtaactgtt tgctggacct    1440
accacgaaag cagatcctgg cgggactac aaggacgac gatgacaagg ggtagaagct      1500
tgtcgagaag tactag                                                     1516
```

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (13)
<223> OTHER INFORMATION: Dabcyl-Lys

<400> SEQUENCE: 3

Glu Lys Glu Leu Ala Glu Leu Arg Glu Ser Thr Ser Lys
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (13)
<223> OTHER INFORMATION: Dabcyl-Lys

<400> SEQUENCE: 4

Glu Ala Asp Leu Ser Ser Phe Lys Ser Gln Glu Leu Lys
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (11)
<223> OTHER INFORMATION: Dabcyl-Lys

<400> SEQUENCE: 5

Glu Lys Ala Arg Val Leu Ala Glu Ala Ala Lys
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (11)
<223> OTHER INFORMATION: Dabcyl-Lys

<400> SEQUENCE: 6

Glu Lys Ala Arg Val Leu Ala Glu Ala Met Lys
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (14)
<223> OTHER INFORMATION: Dabcyl-Lys

<400> SEQUENCE: 7

Glu Arg Ala Glu Gln Gln Arg Leu Lys Ser Gln Asp Leu Lys
 1               5                  10
```

```
<210> SEQ ID NO 8
<211> LENGTH: 447
<212> TYPE: PRT
<213> ORGANISM: Homo sapiens

<400> SEQUENCE: 8
```

Met Ser Gln Thr Gly Ser His Pro Gly Arg Gly Leu Ala Gly Arg Trp
1               5                   10                  15

Leu Trp Gly Ala Gln Pro Cys Leu Leu Pro Ile Val Pro Leu Ser
            20                  25                  30

Trp Leu Val Trp Leu Leu Leu Leu Leu Ala Ser Leu Leu Pro Ser
            35                  40                  45

Ala Arg Leu Ala Ser Pro Leu Pro Arg Glu Glu Ile Val Phe Pro
        50                  55                  60

Glu Lys Leu Asn Gly Ser Val Leu Pro Gly Ser Gly Thr Pro Ala Arg
65              70                  75                  80

Leu Leu Cys Arg Leu Gln Ala Phe Gly Glu Thr Leu Leu Glu Leu
                85                  90                  95

Glu Gln Asp Ser Gly Val Gln Val Glu Gly Leu Thr Val Gln Tyr Leu
            100                 105                 110

Gly Gln Ala Pro Glu Leu Leu Gly Ala Glu Pro Gly Thr Tyr Leu
        115                 120                 125

Thr Gly Thr Ile Asn Gly Asp Pro Glu Ser Val Ala Ser Leu His Trp
    130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Arg Pro Arg
                195                 200                 205

Arg Ala Lys Arg Phe Ala Ser Leu Ser Arg Phe Val Glu Thr Leu Val
        210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270

Gly Ser Gly Glu Glu Gly Pro Gln Val Gly Pro Ser Ala Ala Gln Thr
        275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
            340                 345                 350

Leu Gln Ser Ala Phe Thr Ala Ala His Glu Leu Gly His Val Phe Asn
        355                 360                 365

Met Leu His Asp Asn Ser Lys Pro Cys Ile Ser Leu Asn Gly Pro Leu
    370                 375                 380

-continued

```
Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
            405                 410                 415

Asp Asn Gly Tyr Gly His Cys Leu Leu Asp Lys Pro Glu Ala Pro Leu
            420                 425                 430

His Leu Pro Val Thr Gly Asp Tyr Lys Asp Asp Asp Lys Gly
        435                 440                 445
```

<210> SEQ ID NO 9
<211> LENGTH: 492
<212> TYPE: PRT
<213> ORGANISM: Homo sapiens

<400> SEQUENCE: 9

```
Met Leu Leu Gly Trp Ala Ser Leu Leu Cys Ala Phe Arg Leu Pro
1               5                   10                  15

Leu Ala Ala Val Gly Pro Ala Ala Thr Pro Ala Gln Asp Lys Ala Gly
            20                  25                  30

Gln Pro Pro Thr Ala Ala Ala Ala Gln Pro Arg Arg Arg Gln Gly
        35                  40                  45

Glu Glu Val Gln Glu Arg Ala Glu Pro Pro Gly His Pro His Pro Leu
    50                  55                  60

Ala Gln Arg Arg Arg Ser Lys Gly Leu Val Gln Asn Ile Asp Gln Leu
65                  70                  75                  80

Tyr Ser Gly Gly Gly Lys Val Gly Tyr Leu Val Tyr Ala Gly Gly Arg
                85                  90                  95

Arg Phe Leu Leu Asp Leu Glu Arg Asp Gly Ser Val Gly Ile Ala Gly
            100                 105                 110

Phe Val Pro Ala Gly Gly Gly Thr Ser Ala Pro Trp Arg His Arg Ser
        115                 120                 125

His Cys Phe Tyr Arg Gly Thr Val Asp Gly Ser Pro Arg Ser Leu Ala
    130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
    210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
    290                 295                 300

Ala Ser Ile Glu Asn His Ile Arg Leu Ala Val Val Lys Val Val Val
```

```
                305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
                340                 345                 350

Asp Asp His Glu Glu His Tyr Asp Ala Ala Ile Leu Phe Thr Arg Glu
                355                 360                 365

Asp Leu Cys Gly His His Ser Cys Asp Thr Leu Gly Met Ala Asp Val
            370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Thr Phe Gly Ser
                420                 425                 430

Thr Glu Asp Lys Arg Leu Met Ser Ser Ile Leu Thr Ser Ile Asp Ala
            435                 440                 445

Ser Lys Pro Trp Ser Lys Cys Thr Ser Ala Thr Ile Thr Glu Phe Leu
    450                 455                 460

Asp Asp Gly His Gly Asn Cys Leu Leu Asp Leu Pro Arg Lys Gln Ile
465                 470                 475                 480

Leu Gly Gly Asp Tyr Lys Asp Asp Asp Lys Gly
                485                 490

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (14)
<223> OTHER INFORMATION: Dabcyl-Lys

<400> SEQUENCE: 10

Glu His Ser Asp Ala Val Phe Thr Asp Asn Tyr Thr Arg Lys
 1               5                  10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (5)
<223> OTHER INFORMATION: Dabcyl-Lys

<400> SEQUENCE: 11

Glu Ala Glu Asn Lys
 1               5
```

```
<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 12

Glu Gly Arg His Ile Asp Asn Glu Glu Asp Ile Lys
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (10)
<223> OTHER INFORMATION: Dabcyl-Lys

<400> SEQUENCE: 13

Glu Gly Asn Ala Phe Asn Asn Leu Asp Lys
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 14

Glu Tyr Thr Pro Asn Asn Glu Ile Asp Ser Phe Lys
 1               5                  10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
```

```
<221> NAME/KEY: MOD_RES
<222> LOCATION: (9)
<223> OTHER INFORMATION: Dabcyl-Lys

<400> SEQUENCE: 15

Glu Gln Leu Arg Met Lys Leu Pro Lys
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (9)
<223> OTHER INFORMATION: Dabcyl-Lys

<400> SEQUENCE: 16

Glu Arg Gly Phe Phe Tyr Thr Pro Lys
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (9)
<223> OTHER INFORMATION: Dabcyl-Lys

<400> SEQUENCE: 17

Glu Val Thr Glu Gly Pro Ile Pro Lys
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (9)
<223> OTHER INFORMATION: Dabcyl-Lys

<400> SEQUENCE: 18

Glu Pro Leu Phe Tyr Glu Ala Pro Lys
 1               5

<210> SEQ ID NO 19
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (9)
<223> OTHER INFORMATION: Dabcyl-Lys

<400> SEQUENCE: 19

Glu Leu Pro Met Gly Ala Leu Pro Lys
 1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (10)
<223> OTHER INFORMATION: Dabcyl-Lys

<400> SEQUENCE: 20

Glu Lys Pro Ala Ala Phe Phe Arg Leu Lys
 1               5                  10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (14)
<223> OTHER INFORMATION: Dabcyl-Lys

<400> SEQUENCE: 21

Glu Leu Tyr Glu Asn Lys Pro Arg Arg Pro Tyr Ile Leu Lys
 1               5                  10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (11)
<223> OTHER INFORMATION: Dabcyl-Lys
```

-continued

```
<400> SEQUENCE: 22

Glu Ser Glu Val Asn Leu Asp Ala Glu Phe Lys
 1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (10)
<223> OTHER INFORMATION: Dabcyl-Lys

<400> SEQUENCE: 23

Glu Ser Gln Asn Tyr Pro Ile Val Gln Lys
 1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (10)
<223> OTHER INFORMATION: Dabcyl-Lys

<400> SEQUENCE: 24

Glu Lys Pro Ile Glu Phe Phe Arg Leu Lys
 1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (10)
<223> OTHER INFORMATION: Dabcyl-Lys

<400> SEQUENCE: 25

Glu Lys Pro Ala Glu Phe Phe Ala Leu Lys
 1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (10)
<223> OTHER INFORMATION: Dabcyl-Lys

<400> SEQUENCE: 26

Glu Lys Pro Ala Lys Phe Phe Arg Leu Lys
 1               5                  10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 27

Arg Glu Ile Pro Phe His Leu Val Ile His Thr Lys Arg
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 28

Glu Met Ala Pro Gly Ala Val His Leu Pro Gln Lys
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 29

Glu Pro Leu Ala Gln Ala Val Arg Ser Ser Ser Lys
 1               5                  10
```

```
<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 30

Glu Pro Pro Val Ala Ala Ser Ser Leu Arg Asn Lys
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 31

Glu Pro Gln Ile Glu Asn Val Lys Gly Thr Glu Lys
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 32

Glu Ser Leu Pro Val Gln Asp Ser Ser Ser Val Lys
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
```

```
<220> FEATURE:
<221> NAME/KEY: MOD_RES
<222> LOCATION: (12)
<223> OTHER INFORMATION: Dabcyl-Lys

<400> SEQUENCE: 33

Glu Val His His Gln Lys Leu Val Phe Phe Ala Lys
 1               5                  10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dabcyl-Lys
<220> FEATURE:
<221> NAME/KEY: MOD_RES
<222> LOCATION: (14)
<223> OTHER INFORMATION: Aedans-Glu

<400> SEQUENCE: 34

Lys Arg Gly Val Val Asn Ala Ser Ser Arg Leu Ala Lys Glu
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dabcyl-Lys
<220> FEATURE:
<221> NAME/KEY: MOD_RES
<222> LOCATION: (10)
<223> OTHER INFORMATION: Aedans-Glu

<400> SEQUENCE: 35

Lys Leu Val Leu Ala Ser Ser Ser Phe Glu
 1               5                  10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dabcyl-Lys
<220> FEATURE:
<221> NAME/KEY: MOD_RES
<222> LOCATION: (14)
<223> OTHER INFORMATION: Aedans-Glu

<400> SEQUENCE: 36

Lys Ser Asn Arg Leu Glu Ala Ser Ser Arg Ser Ser Pro Glu
 1               5                  10

<210> SEQ ID NO 37
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (7)
<223> OTHER INFORMATION: aminobutyric acid
<220> FEATURE:
<221> NAME/KEY: MOD_RES
<222> LOCATION: (14)
<223> OTHER INFORMATION: Dabcyl-Lys

<400> SEQUENCE: 37

Glu Asp Glu Met Glu Glu Xaa Ala Ser His Leu Pro Tyr Lys
  1               5                  10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (14)
<223> OTHER INFORMATION: Dabcyl-Lys

<400> SEQUENCE: 38

Glu Ala Gly Pro Arg Gly Met Ala Gly Gln Phe Ser His Lys
  1               5                  10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dabcyl-Lys
<220> FEATURE:
<221> NAME/KEY: MOD_RES
<222> LOCATION: (9)
<223> OTHER INFORMATION: Aedans-Glu

<400> SEQUENCE: 39

Lys Arg Pro Leu Gly Leu Ala Arg Glu
  1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
```

```
<220> FEATURE:
<221> NAME/KEY: MOD_RES
<222> LOCATION: (11)
<223> OTHER INFORMATION: Dabcyl-Lys

<400> SEQUENCE: 40

Glu Gly Tyr Tyr Ser Arg Asp Met Leu Val Lys
 1               5                  10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 41

Glu Gln Lys Leu Asp Lys Ser Phe Ser Met Ile Lys
 1               5                  10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (13)
<223> OTHER INFORMATION: Dabcyl-Lys

<400> SEQUENCE: 42

Glu Pro Ser Ala Ala Gln Thr Ala Arg Gln His Pro Lys
 1               5                  10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 43

Glu Pro Gly Ala Gln Gly Leu Pro Gly Val Gly Lys
 1               5                  10

<210> SEQ ID NO 44
<211> LENGTH: 8
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Leu Arg Thr Asn Ser Phe Ser
 1               5

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Gly Val Val Asn Ala Ser Ser Arg Leu Ala
 1               5                  10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Aedans-Lys
<220> FEATURE:
<221> NAME/KEY: MOD_RES
<222> LOCATION: (13)
<223> OTHER INFORMATION: Dabcyl-Glu

<400> SEQUENCE: 46

Glu Asp Lys Pro Ile Leu Phe Phe Arg Leu Gly Lys Glu
 1               5                  10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (14)
<223> OTHER INFORMATION: Dabcyl-Lys

<400> SEQUENCE: 47

Glu Met His Thr Ala Ser Ser Leu Glu Lys Gln Ile Gly Lys
 1               5                  10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 48

Glu Arg Phe Ala Gln Ala Gln Gln Gln Leu Pro Lys
 1               5                  10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (14)
<223> OTHER INFORMATION: Dabcyl-Lys

<400> SEQUENCE: 49

Glu Lys Lys Glu Asn Ser Phe Glu Met Gln Gly Asp Gln Lys
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Ala Gln Ala Val Arg Ser Ser Ser Arg
 1               5                  10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (10)
<223> OTHER INFORMATION: Dabcyl-Lys

<400> SEQUENCE: 51

Glu Arg Thr Ala Ala Val Phe Arg Pro Lys
 1               5                  10

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (9)
<223> OTHER INFORMATION: Dabcyl-Lys

<400> SEQUENCE: 52

Glu Arg Val Arg Arg Ala Leu Pro Lys
 1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (10)
<223> OTHER INFORMATION: Dabcyl-Lys

<400> SEQUENCE: 53

Glu Ser Phe Pro Arg Met Phe Ser Asp Lys
 1               5                  10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (12)
<223> OTHER INFORMATION: Dabcyl-Lys

<400> SEQUENCE: 54

Glu Glu Tyr Leu Glu Ser Phe Leu Glu Arg Pro Lys
 1               5                  10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (13)
<223> OTHER INFORMATION: Dabcyl-Lys

<400> SEQUENCE: 55

Glu Arg Pro Lys Pro Gln Gln Phe Phe Gly Leu Met Lys
 1               5                  10
```

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (14)
<223> OTHER INFORMATION: Dabcyl-Lys

<400> SEQUENCE: 56

Glu His Gly Asp Gln Met Ala Gln Lys Ser Gln Ser Thr Lys
 1               5                  10

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (16)
<223> OTHER INFORMATION: Dabcyl-Lys

<400> SEQUENCE: 57

Glu Arg Asn Ile Thr Glu Gly Glu Ala Arg Gly Ser Val Ile Leu Lys
 1               5                  10                  15

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (11)
<223> OTHER INFORMATION: Dabcyl-Lys

<400> SEQUENCE: 58

Glu Ala Gly Gln Arg Leu Ala Thr Ala Met Lys
 1               5                  10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:

```
<221> NAME/KEY: MOD_RES
<222> LOCATION: (13)
<223> OTHER INFORMATION: Dabcyl-Lys

<400> SEQUENCE: 59

Glu Val Gly Leu Met Gly Lys Arg Ala Leu Asn Ser Lys
 1               5                  10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Aedans-Glu
<220> FEATURE:
<221> NAME/KEY: MOD_RES
<222> LOCATION: (13)
<223> OTHER INFORMATION: Dabcyl-Lys

<400> SEQUENCE: 60

Glu Lys Glu Asp Gly Glu Ala Arg Ala Ser Thr Ser Lys
 1               5                  10
```